United States Patent
Brown et al.

(10) Patent No.: US 6,506,954 B1
(45) Date of Patent: Jan. 14, 2003

(54) PROCESS FOR PRODUCING CHEMICALS FROM OXYGENATE

(75) Inventors: Stephen H. Brown, Princeton; Larry A. Green, Mickleton, both of NJ (US); Mark F. Mathias, Pitsford, NY (US); David H. Olson, Pennington, NJ (US); Robert A. Ware, Wyndmoor, PA (US); William A. Weber, Burlington, NJ (US); Reuel Shinnar, Great Neck, NY (US)

(73) Assignee: Exxon Mobil Chemical Patents, Inc., Houston, TX (US)

( * ) Notice: Subject to any disclaimer, the term of this patent is extended or adjusted under 35 U.S.C. 154(b) by 0 days.

(21) Appl. No.: 09/687,749

(22) Filed: Oct. 13, 2000

Related U.S. Application Data

(63) Continuation-in-part of application No. 09/547,093, filed on Apr. 11, 2000, now abandoned.

(51) Int. Cl.[7] .................................................. C07C 1/20
(52) U.S. Cl. ........................ 585/640; 585/634; 585/469
(58) Field of Search ................................ 585/640, 639, 585/469

(56) References Cited

U.S. PATENT DOCUMENTS

| | | | |
|---|---|---|---|
| 3,702,886 A | 11/1972 | Argauer et al. | 423/328 |
| 3,709,979 A | 1/1973 | Chu | 423/328 |
| 3,832,449 A | 8/1974 | Rosinski et al. | 423/328 |
| 4,016,218 A | 4/1977 | Haag et al. | 260/671 |
| 4,016,245 A | 4/1977 | Plank et al. | 423/328 |
| 4,025,571 A | 5/1977 | Lago | 260/668 |

(List continued on next page.)

FOREIGN PATENT DOCUMENTS

| | | | |
|---|---|---|---|
| EP | 0026 041 A1 | 4/1981 | |
| EP | 123 449 A1 | 10/1984 | |
| EP | 0882692 | 12/1998 | C07C/1/20 |
| WO | WO 99/51548 | 10/1999 | C07C/1/00 |

OTHER PUBLICATIONS

Mole et al., *Conversion of Methanol to Hyrdocarbons over ZSM–5 Zeolite: An Examination of the Role of Aromatic Hydrocardons Using Carbon– and Deuterium–Labeled Feeds*, Journal of Catalysis, 84, pp. 435–445 (1983).

Crank, *The Mathematics of Diffusion*, Oxford University Press, Ely House, London, (1967).

(List continued on next page.)

*Primary Examiner*—Thuan D. Dang
(74) *Attorney, Agent, or Firm*—Paul T. La Voie

(57) ABSTRACT

There is provided a process for converting methanol and/or dimethyl ether to a product containing olefin, e.g., $C_2$ to $C_4$ olefins, $C_{9+}$ aromatics and non-$C_{9+}$ aromatics which comprises:

Figure 1:
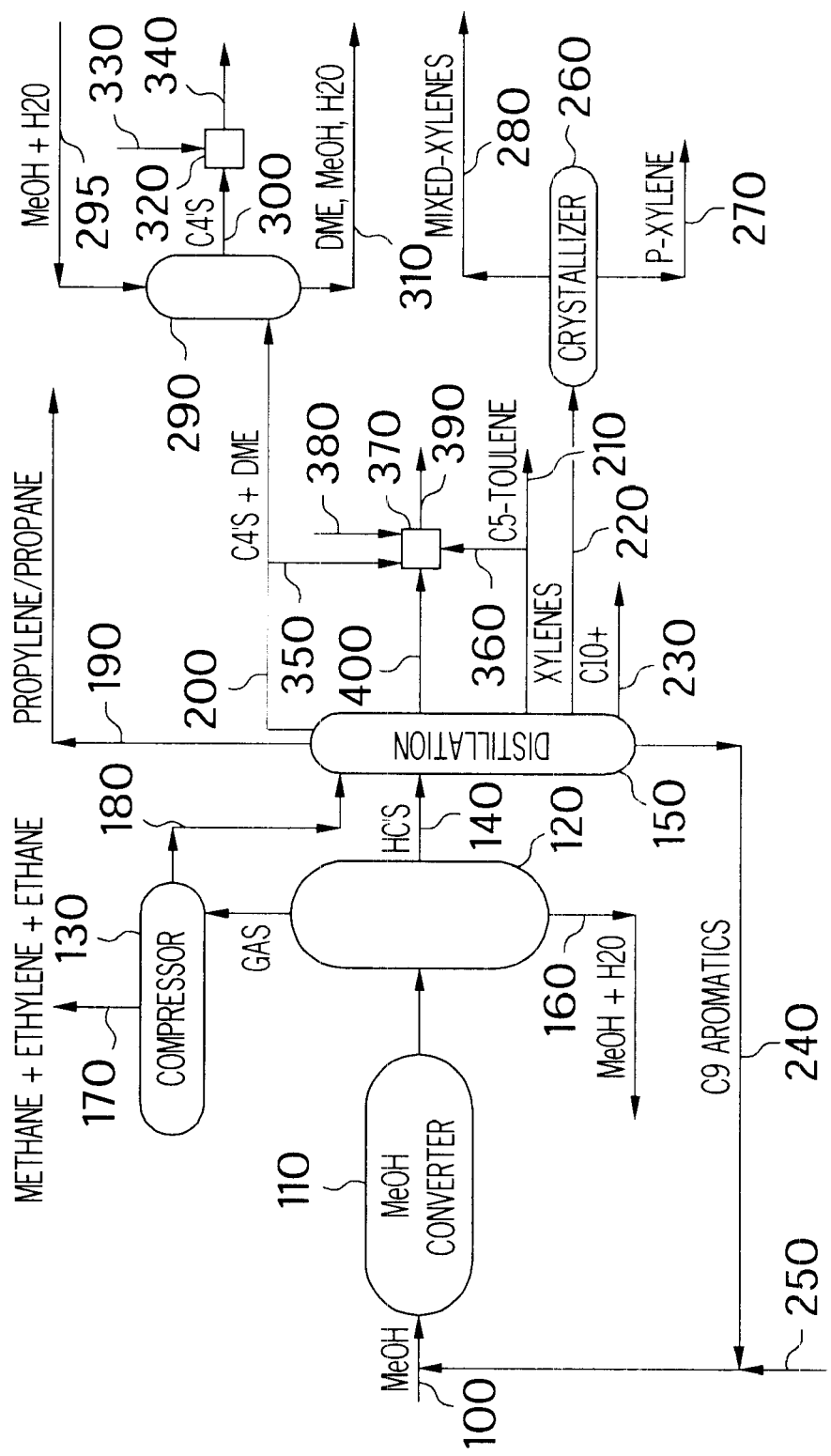

1) contacting a feed which contains methanol and/or dimethyl ether with a catalyst comprising a porous crystalline material, said contacting step being conducted in the presence of aromatics comprising $C_9$ or $C_{9+}$ aromatic compound produced in said process under conversion conditions including a temperature of 350° C. to 480° C. and a methanol partial pressure in excess of 10 psia (70 kPa), said porous crystalline material having a Diffusion Parameter for 2,2-dimethylbutane of about 0.1 sec$^{-1}$ to about 20 sec$^{-1}$ when measured at a temperature of 120° C. and a 2,2-dimethylbutane pressure of 60 torr (8 kPa), and the aromatics being capable of alkylation by the methanol and/or dimethyl ether under said conversion conditions to provide a stream which contains $C_2$ to $C_4$ olefins and $C_9$ or $C_{9+}$ aromatic compound;

2) separating said stream to form a substantially $C_2$ to $C_4$ olefin product stream and a substantially $C_9$ or $C_{9+}$ aromatic compound stream; and 3) recycling at least a portion of said substantially $C_9$ or $C_{9+}$ aromatic compound stream to step 1).

36 Claims, 2 Drawing Sheets

U.S. PATENT DOCUMENTS

| | | | |
|---|---|---|---|
| 4,025,572 A | 5/1977 | Lago | 260/668 |
| 4,025,575 A | 5/1977 | Chang et al. | 260/682 |
| 4,038,889 A | 8/1977 | Lindow et al. | 74/866 |
| 4,076,842 A | 2/1978 | Plank et al. | 423/328 |
| 4,079,095 A | 3/1978 | Givens et al. | 260/682 |
| 4,083,888 A | 4/1978 | Caesar et al. | 200/682 |
| 4,083,889 A | 4/1978 | Caesar et al. | 260/682 |
| 4,097,543 A | 6/1978 | Haag et al. | 260/672 T |
| 4,296,266 A | 10/1981 | Wunder et al. | 585/640 |
| 4,324,940 A | 4/1982 | Dessau | 585/466 |
| 4,356,338 A | 10/1982 | Young | 585/407 |
| 4,374,295 A | 2/1983 | Lee | 585/640 |
| 4,375,573 A | 3/1983 | Young | 585/467 |
| 4,423,273 A | 12/1983 | Hoelderich et al. | 585/640 |
| 4,433,188 A | 2/1984 | Hoelderich et al. | 585/640 |
| 4,433,189 A | 2/1984 | Young | 585/640 |
| 4,434,314 A | 2/1984 | Hoelderich et al. | 585/640 |
| 4,440,871 A | 4/1984 | Lok et al. | 502/214 |
| 4,441,990 A | 4/1984 | Huang | 208/111 |
| 4,480,145 A | 10/1984 | Brennan et al. | 585/640 |
| 4,496,786 A | 1/1985 | Santilli et al. | 585/640 |
| 4,499,314 A | 2/1985 | Seddon et al. | 585/408 |
| 4,499,327 A | 2/1985 | Kaiser | 585/640 |
| 4,547,616 A | 10/1985 | Avidan et al. | 585/640 |
| 4,550,217 A | 10/1985 | Graziani et al. | 585/324 |
| 4,582,815 A | 4/1986 | Bowes | 502/64 |
| 4,616,098 A | 10/1986 | Hoelderich et al. | 585/640 |
| 4,665,268 A | 5/1987 | Lee et al. | 585/640 |
| 4,677,242 A | 6/1987 | Kaiser | 585/638 |
| 4,677,243 A | 6/1987 | Kaiser | 585/638 |
| 4,698,452 A | 10/1987 | Le Van Mao et al. | 585/640 |
| 4,752,651 A | 6/1988 | Kaiser | 585/640 |
| 4,767,886 A | 8/1988 | Kawamura et al. | 585/640 |
| 4,777,321 A | 10/1988 | Harandi et al. | 585/640 |
| 4,861,939 A | 8/1989 | Debras et al. | 585/640 |
| 4,912,281 A | 3/1990 | Wu | 585/640 |
| 5,043,503 A | 8/1991 | Del Rossi et al. | 585/360 |
| 5,053,374 A | 10/1991 | Absil et al. | 502/64 |
| 5,095,163 A | 3/1992 | Barger | 585/640 |
| 5,095,167 A | 3/1992 | Christensen | 585/720 |
| 5,110,776 A | 5/1992 | Chitnis et al. | 502/64 |
| 5,182,242 A | 1/1993 | Marler | 502/66 |
| 5,191,141 A | 3/1993 | Barger et al. | 585/640 |
| 5,191,142 A | 3/1993 | Marshall et al. | 585/640 |
| 5,231,064 A | 7/1993 | Absil et al. | 502/68 |
| 5,250,277 A | 10/1993 | Kresge et al. | 423/329.1 |
| 5,278,345 A | 1/1994 | Janssen et al. | 585/640 |
| 5,304,698 A | 4/1994 | Husain | 585/722 |
| 5,714,662 A | 2/1998 | Vora et al. | 585/640 |
| 5,714,663 A | 2/1998 | Serrand et al. | 585/648 |
| 6,040,257 A | 3/2000 | Drake et al. | 502/64 |

OTHER PUBLICATIONS

Olson et al. *Chemical and Physical Properties of the ZSM–5 Substitutional Series*, Journal of Catalysis 61, pp. 390–396 (1980).

Chang, "Methanol Conversion to Light Olefins," Catal. Rev.–Sci. Eng., 26(3&4), 323–345 (1984).

Kaeding et al., "Production of Chemicals from Methanol," Journal of Catalysis 61, 155–164 (1980).

Barger et al. "Converting Natural Gas to Ethylene and Propylene by the UOP/Hydro MTO Process," 12$^{th}$ International Zeolite Conference Materials Research Society pp. 567–573 (1999).

PROCESS FOR PRODUCING CHEMICALS FROM OXYGENATE

RELATED APPLICATIONS

This application is a continuation-in-part of U.S. application Ser. No. 09/547,093, filed Apr. 11, 2000, now abandoned, the entire disclosure of which is expressly incorporated herein by reference.

BACKGROUND OF THE INVENTION

The present invention relates to a process for producing light olefins rich in ethylene from a feedstream of methanol and dimethyl ether combined with $C_9$ or $C_{9+}$ aromatics produced by the process.

A remarkable growth in the production of synthetic fibers, plastics and rubber has taken place in recent decades. This growth, to a very large extent, has been supported and encouraged by an expanding supply of inexpensive petrochemical raw materials such as ethylene, propylene, and other, four and five carbon olefins. Side by side with this growth, there has been an increasing demand for alkylate, made by reacting olefins with isobutane, for use as a high octane gasoline component.

Burgeoning demand for olefins, particularly ethylene, propylene and butenes, has of course led to periods of shortage, which has led to substantial price increases in the feedstocks to the commercialized technologies. These feedstocks are largely C2 to C4 paraffins co-produced with natural gas and/or paraffinic straight run naphtha. These feedstocks can be substantially more expensive than methane, making it desirable to provide efficient means for converting methane to olefins.

Conversion of methane to methanol followed by conversion of methanol to light olefins is among the most economic routes to make light olefins from methane. In this respect, it is known that methanol or methyl ether can be catalytically converted to olefin-containing hydrocarbon mixtures by contact under certain conditions with particular types of crystalline zeolite materials. U.S. Pat. Nos. 4,025,575 and 4,038,889 for example, both disclose processes whereby methanol and/or methyl ether can be converted to an olefin-containing product over a Constraint Index 1–12 zeolite catalyst, particularly ZSM-5. ZSM-5, in fact, converts methanol and/or methyl ether to hydrocarbons containing a relatively high concentration of light olefins with prolonged catalyst lifetime before catalyst regeneration becomes necessary.

It has also been reported that other types of zeolite catalysts can be used to convert methanol and/or methyl ether to olefin-containing hydrocarbons products containing even higher proportions of light olefins than obtained with ZSM-5. For example, U.S. Pat. No. 4,079,095 to Givens, Plank and Rosinski disclose that zeolites of the erionite-offretite-chabazite type, and especially ZSM-34, can usefully be employed to promote conversion of methanol and/or methyl ether to products comprising a major amount of ethylene and propylene. However, while erionite-offretite-chabazite type catalysts are highly selective to light olefins production, such smaller pore zeolites tend to age rapidly in comparison to ZSM-5 when used for methanol/methyl ether conversion.

U.S. Pat. Nos. 4,677,242 and 4,752,651 disclose the conversion of methanol to $C_2$–$C_4$ olefins over various silicoaluminophosphates and "non-zeolitic molecular sieves" (such as metal aluminophosphates) and teach that the addition of diluents, such as aromatic materials, having a kinetic diameter greater than the pore size of the molecular sieve increases the ethylene to propylene ratio in the product.

T. Mole, G. Bett, and D. J. Seddon, *Journal of Catalysis* 84, 435 (1983), disclose that the presence of aromatic compounds can accelerate the zeolite-catalyzed conversion of methanol to hydrocarbons. The article reports ethylene yields of 5–22% when methanol is catalytically converted in the presence of benzene or toluene over ZSM-5 at sub-atmospheric pressure, 279 to 350° C., and 100% methanol conversion.

U.S. Pat. No. 4,499,314 discloses that the addition of various promoters, including aromatic compounds, such as toluene, accelerate the conversion of methanol to hydrocarbons over zeolites, such as ZSM-5, which have a pore size sufficient to permit sorption and diffusion of the promoter. In particular, the '314 patent teaches that the increased conversion resulting from the addition of the promoter allows the use of lower severity conditions, particularly lower temperatures, which increase the yield of lower olefins (column 4, lines 17–22). Thus in Example 1 of the patent the addition of toluene as a promoter reduces the temperature required to achieve full methanol conversion from 295° C. to 288° C. while increasing the ethylene yield from 11 wt. % to 18 wt. %. In the Examples of the '349 patent the methanol feedstock is diluted with water and nitrogen such that the methanol partial pressure is less than 2 psia.

U.S. Pat. No. 6,046,372, to Brown et al. discloses a process for converting methanol and an aromatic co-feed which may include C9+ reformate streams.

In spite of the existence of methanol conversion processes utilizing a variety of zeolite catalysts and process conditions, there is a continuing need to develop new procedures suitable to convert an organic charge comprising methanol and/or dimethyl ether selectively to light olefin products in the presence of an aromatic co-feed, and in particular, ethylene. An object of the present invention is therefore to address this need, particularly, where the process produces heavier aromatic by-products, e.g., $C_{9+}$ aromatics. It would be especially useful for methanol conversion processes utilizing aromatic co-feed to employ a source of aromatics derived from the products of the process itself, i.e., a recycle stream, which essentially provides a self-contained process which does not require an outside source of aromatics.

SUMMARY OF THE INVENTION

In one aspect, the present invention relates to a process for converting methanol and/or dimethyl ether to a product containing $C_2$ to $C_4$ olefins which comprises:

1) contacting a feed which contains methanol and/or dimethyl ether with a catalyst comprising a porous crystalline material, said contacting step being conducted in the presence of aromatics comprising $C_9$ or $C_{9+}$ aromatic compound produced in said process under conversion conditions including a temperature of 350° C. to 480° C. and a methanol partial pressure in excess of 10 psia (70 kPa), said porous crystalline material having a Diffusion Parameter for 2,2-dimethylbutane of about 0.1–20 sec$^{-1}$ when measured at a temperature of 120° C. and a 2,2-dimethylbutane pressure of 60 torr (8 kPa), and the aromatics being capable of alkylation by the methanol and/or dimethyl ether under said conversion conditions to provide a stream which contains $C_2$ to $C_4$ olefins and $C_9$ or $C_{9+}$ aromatic compound;

2) separating said stream to form a substantially $C_2$ to $C_4$ olefin product stream and a substantially $C_9$ or $C_{9+}$ aromatic compound stream; and 3) recycling at least a portion of said substantially $C_9$ or $C_{9+}$ aromatic compound stream to step 1).

In another aspect, the present invention relates to a process for converting methanol and/or dimethyl ether to a product comprising olefins, $C_{9+}$ aromatics and non-$C_{9+}$ aromatics which comprises:

i) combining a feedstream which contains methanol and/or dimethyl ether with a feedstream substantially comprising $C_9$ or $C_{9+}$ aromatics produced in said process to provide a mixed feed;

ii) contacting said mixed feed in an oxygenate conversion zone with a catalyst comprising a porous crystalline material, said contacting step being conducted under conversion conditions including a temperature of 350° C. to 480° C. and a methanol partial pressure in excess of 10 psia (70 kPa), said porous crystalline material having a pore size greater than the critical diameter of toluene, and at least some of said $C_9$ or $C_{9+}$ aromatics being capable of alkylation by the methanol and/or dimethyl ether under said conversion conditions, to provide a product containing olefins, $C_9$ or $C_{9+}$ aromatics and non-$C_9$ or non-$C_{9+}$ aromatics;

iii) separating $C_9$ or $C_{9+}$ aromatics from said product to provide a feedstream substantially comprising $C_9$ or $C_{9+}$ aromatics;

iv) recycling to step i) at least some of said feedstream substantially comprising $C_9$ or $C_{9+}$ aromatics;

v) separating said olefins from said product to provide a stream substantially comprising olefins; and vi) separating said non-$C_9$ or non-$C_{9+}$ aromatics from said product to provide a stream substantially comprising non-$C_9$ or non-$C_{9+}$ aromatics.

The order of steps iii), v) and vi) relative to each other is not critical. In other words, the product of oxygenate conversion can be treated to remove $C_9$ or $C_{9+}$ aromatics, olefins, or non-$C_9$ or non-$C_{9+}$ aromatics, in any order or even simultaneously.

In a preferred embodiment, the process may further comprise: vii) purging said feedstream substantially comprising $C_9$ or $C_{9+}$ aromatics to an extent sufficient to prevent undesirable accumulation of unreactive $C_{9+}$ aromatics in the mixed feed.

In another preferred embodiment, the non-$C_9$ or non-$C_{9+}$ aromatics of step ii) comprise mixed xylenes which are separated out to provide a substantially mixed xylene-containing stream which is subsequently treated to provide a substantially p-xylene-containing stream.

In yet another aspect, the present invention relates to a process for converting methanol and/or dimethyl ether to a product comprising olefins, $C_{9+}$ aromatics and non-$C_{9+}$ aromatics which comprises:

a) combining a feedstream which contains methanol and/or dimethyl ether with a feedstream substantially comprising $C_9$ or $C_{9+}$ aromatics produced in said process to provide a mixed feed;

b) contacting said mixed feed in an oxygenate conversion zone with a catalyst comprising a porous crystalline material, said contacting step being conducted under conversion conditions including a temperature of 350° C. to 480° C. and a methanol partial pressure in excess of 10 psia (70 kPa), said porous crystalline material having a pore size greater than the critical diameter of toluene, and at least some of said $C_9$ or $C_{9+}$ aromatics being capable of alkylation by the methanol and/or dimethyl ether under said conversion conditions, to provide a product containing olefins, $C_9$ or $C_{9+}$ aromatics and non-$C_9$ or non-$C_{9+}$ aromatics;

c) separating the product from said conversion zone into a light gas hydrocarbon fraction, a distillable hydrocarbon fraction, and an aqueous methanol fraction;

d) recycling said aqueous methanol fraction to step a);

e) compressing said light gas hydrocarbon fraction to provide a $C_1$–$C_2$ hydrocarbon fraction and $C_{3+}$ hydrocarbon fraction;

f) collecting said $C_1$–$C_2$ hydrocarbon fraction;

g) introducing said $C_{3+}$ hydrocarbon fraction and said distillable hydrocarbon fraction to a distillation column and withdrawing a $C_3$ hydrocarbon overheads fraction, a $C_4$ hydrocarbon and dimethyl ether fraction, a $C_5$ hydrocarbon-toluene fraction, a mixed xylenes fraction, a $C_9$ aromatics fraction and a $C_{10+}$ aromatics fraction;

h) treating said $C_4$ hydrocarbon and dimethyl ether fraction with water and/or said aqueous methanol to provide a substantially $C_4$ hydrocarbon stream which comprises $C_4$ olefins and a substantially dimethyl ether-, methanol-, and water-containing stream;

i) recycling said substantially dimethylether-, methanol-, and water-containing stream to step a); and j) treating said mixed xylenes fraction, e.g., in a crystallizer or Parex, to provide a substantially p-xylene containing effluent stream and a mixed xylenes-containing effluent stream substantially comprising ethylbenzene, o-xylene and m-xylene.

In a preferred embodiment, the process further comprises alkylating said substantially $C_4$ hydrocarbon stream containing $C_4$ olefins by contacting with an alkylating agent selected from the group consisting of isobutane and isopentane under olefin alkylating conditions to provide an alkylate-containing product.

In another preferred embodiment, the process comprises alkylating said $C_5$ hydrocarbon-toluene fraction containing $C_5$ olefins by contacting with an alkylating agent selected from the group consisting of isobutane and isopentane under olefin alkylating conditions to provide an alkylate-containing product.

In still another preferred embodiment, the process comprises etherifying said $C_4$ hydrocarbon stream containing $C_4$ iso-olefins by contacting with methanol etherifying agent under etherification conditions to provide a product containing tert-butyl ether.

In yet another preferred embodiment, the process comprises etherifying said $C_5$ hydrocarbon-toluene fraction, containing $C_5$ iso-olefins and $C_6$ iso-olefins, by contacting with methanol etherifying agent under etherification conditions to provide a product containing mixed tert-alkyl ethers.

In still another aspect, the present invention relates to a process for converting methanol and/or dimethyl ether to a product comprising olefins, $C_{9+}$ aromatics and non-$C_{9+}$ aromatics which comprises:

A) combining a feedstream which contains methanol and/or dimethyl ether with a feedstream substantially comprising $C_9$ or $C_{9+}$ aromatics produced in said process to provide a mixed feed;

B) contacting said mixed feed in an oxygenate conversion zone with a catalyst comprising a porous crystalline material, said contacting step being conducted under conversion conditions including a temperature of 350° C. to 480° C. and a methanol partial pressure in excess of 10 psia (70 kPa), said porous crystalline material having a pore size greater than the critical diameter of toluene, and at least some of said $C_9$ or $C_{9+}$ aromatics being capable of alkylation by the methanol and/or dimethyl ether under said conversion conditions, to provide a product containing olefins, $C_9$ or $C_{9+}$ aromatics and non-$C_9$ or non-$C_{9+}$ aromatics;

C) separating the product from said conversion zone into a light gas hydrocarbon fraction, a distillable hydrocarbon fraction, and an aqueous methanol fraction;

D) recycling at least a portion of said aqueous methanol fraction to step A);

E) compressing said light gas hydrocarbon fraction to provide a $C_1$–$C_2$ hydrocarbon fraction and $C_{3+}$ hydrocarbon fraction;

F) collecting said $C_1$–$C_2$ hydrocarbon fraction;

G) introducing said $C_{3+}$ hydrocarbon fraction and said distillable hydrocarbon fraction to a distillation column and withdrawing a $C_3$ hydrocarbon overheads fraction, a $C_4$ hydrocarbon-toluene and dimethyl ether fraction comprising $C_4$–$C_6$ iso-olefins, a mixed xylenes fraction, a $C_9$ aromatics fraction and a $C_{10+}$ aromatics fraction;

H) etherifying said $C_4$ hydrocarbon-toluene and dimethylether fraction comprising $C_4$–$C_6$ iso-olefins by contacting with aqueous methanol under etherification conditions to provide an effluent stream which comprises an aqueous phase comprising mixed tert-alkylethers, dimethylether, methanol and water, and an organic phase comprising toluene which is recyclable to step A); and I) separating said aqueous phase into a substantially mixed tert-alkylether fraction, and a dimethylether-, methanol- and water-containing fraction which is recyclable to step A).

Preferably, the olefins comprise $C_2$ to $C_4$ olefins.

Preferably, the molar ratio of methanol and/or dimethyl ether to $C_9$ or $C_{9+}$ aromatics is greater than 5:1 and preferably is less than 300:1. More preferably, the molar ratio of methanol and/or dimethyl ether to $C_9$ or $C_{9+}$ aromatics compound is from 10:1 to 250:1.

Preferably, the conversion conditions include a temperature of 400° C. to 460° C.

Preferably, the conversion conditions are such that the methanol conversion rate is less than 90% and more preferably less than 80%.

Preferably, the porous crystalline material has a pore size of 5 to 7 Angstrom.

Preferably, the porous crystalline material is an aluminosilicate zeolite and most preferably is ZSM-5.

Preferably, the catalyst has an alpha value less than 50 and more preferably less than 10.

Preferably, the porous crystalline material has a Diffusion Parameter for 2,2-dimethylbutane of about 0.1 $sec^{-1}$ to about 20 $sec^{-1}$ when measured at a temperature of 120° C. and a 2,2-dimethylbutane pressure of 60 torr (8 kPa).

Preferably, the porous crystalline material has a Diffusion Parameter of about 0.2 $sec^{-1}$ to about 5 $sec^{-1}$.

Preferably, the catalyst contains coke or an oxide modifier selected from oxides of boron, magnesium, silicon and most preferably phosphorus.

Preferably, the catalyst contains about 0.05 wt. % to about 20 wt. %, and more preferably about 1 wt. % to about 10 wt. %, of the coke or the oxide modifier on an elemental basis.

The present invention resides in a process for converting methanol and/or dimethyl ether to a product containing olefin, e.g., $C_2$ to $C_4$ olefins, $C_{9+}$ aromatics and non-$C_{9+}$ aromatics which comprises:

i) combining a feedstream which contains methanol and/or dimethyl ether with a feedstream substantially comprising $C_9$ or $C_{9+}$ aromatics produced in said process to provide a mixed feed;

ii) contacting said mixed feed in an oxygenate conversion zone with a catalyst comprising a porous crystalline material, said contacting step being conducted under conversion conditions including a temperature of 350° C. to 480° C. and a methanol partial pressure in excess of 10 psia (70 kPa), said porous crystalline material having a pore size greater than the critical diameter of toluene and the toluene being capable of alkylation by the methanol and/or dimethyl ether under said conversion conditions to provide a product containing olefins, $C_{9+}$ aromatics and non-$C_{9+}$ aromatics;

iii) separating out from said product $C_9$ or $C_{9+}$ aromatics to provide a feedstream substantially comprising $C_9$ or $C_{9+}$ aromatics;

iv) recycling to step i) at least some of said feedstream substantially comprising $C_9$ or $C_{9+}$ aromatics; and v) collecting said olefins and said non-$C_9$ or non-$C_{9+}$ aromatics.

Preferably, the olefins comprise $C_2$ to $C_4$ olefins.

Preferably, the process further comprises vi) purging said feedstream substantially comprising $C_9$ or $C_{9+}$ aromatics to an extent sufficient to prevent undesirable accumulation of unreactive $C_{9+}$ aromatics.

Preferably, the molar ratio of methanol and/or dimethyl ether to $C_9$ or $C_{9+}$ aromatics is greater than 5:1 and preferably is less than 300:1. More preferably, the molar ratio of methanol and/or dimethyl ether to $C_9$ or $C_9$ aromatics compound is from 10:1 to 250:1.

Preferably, the conversion conditions include a temperature of 400° C. to 460° C.

Preferably, the conversion conditions are such that the methanol conversion rate is less than 90% and more preferably less than 80%.

Preferably, the porous crystalline material has a pore size between 5 and 7 Angstrom.

Preferably, the porous crystalline material is an aluminosilicate zeolite and most preferably is ZSM-5.

Preferably, the catalyst has an alpha value less than 50 and more preferably less than 10.

Preferably, the porous crystalline material has a Diffusion Parameter for 2,2-dimethylbutane of about 0.1–20 $sec^{-1}$ when measured at a temperature of 120° C. and a 2,2-dimethylbutane pressure of 60 torr (8 kPa).

Preferably, the porous crystalline material has a Diffusion Parameter of about 0.2–5 $sec^{-1}$.

Preferably, the catalyst contains coke or an oxide modifier selected from oxides of boron, magnesium, silicon and most preferably phosphorus.

Preferably, the catalyst contains about 0.05 to about 20 wt. %, and more preferably about 1 to about 10 wt. %, of the coke or the oxide modifier on an elemental basis.

DETAILED DESCRIPTION OF THE INVENTION

The present invention provides a process for selectively converting methanol and/or dimethyl ether to olefins, e.g., $C_2$–$C_4$ olefins, particularly ethylene, over a porous crystalline catalyst and in the presence of an aromatic compound which has a critical diameter less than the pore size of the catalyst and which is capable of alkylation by the methanol and/or dimethyl ether under the conditions of the conversion.

The present invention process is distinguished from that of U.S. Pat. No. 4,499,314 discussed above in that a substantially water-free methanol feed is contacted with a zeolite catalyst, such as ZSM-5, in the presence of a reactive aromatic compound at a relatively high temperature of 350° C. to 480° C. and a relatively high methanol partial pressure in excess of 10 psia (70 kPa). In addition, the process conditions are preferably controlled so that the methanol conversion is less than 90% and more preferably less than 80%. In this way it is found that ethylene selectivities in excess of 30 wt. % can be achieved as compared to the ethylene selectivities of 18–25% by weight reported in the '314 patent.

While not wishing to be bound by any theory of operation, the ethylene selectivity of the process of the invention is believed to follow from our observation that virtually all the ethylene produced via the catalytic partial conversion of methanol to light olefins using zeolite catalysts is derived from the back-cracking of ethyl-aromatic intermediates. The formation of such ethyl-aromatic intermediates is believed to be facilitated in the present process by a mechanism in which the aromatic compound effectively acts as a catalyst in the conversion of two molecules of methanol to one molecule of ethylene. Thus the methylation of aromatics with methanol in zeolites, such as ZSM-5, is a well-known, rapid reaction. The product polymethylbenzenes are stable but are too large to easily exit the pores of the catalyst. Although relatively slow, the next expected reaction of a polymethyl aromatic is skeletal isomerization to a mixed methyl-ethyl aromatic. Once formed, ethyl-aromatics are prone to a rapid cracking reaction to form ethylene and the co-catalytic aromatic ring.

Any methanol feed comprising at least 60 wt. % of methanol may be used to provide methanol for the use in this invention. Substantially pure methanol, such as industrial grade anhydrous methanol, is eminently suitable. Crude methanol, which usually contains from 12 wt. % to 20 wt. % water, or even a more dilute solution, may also be used. However, the presence of water as a diluent to reduce the methanol partial pressure is not required. Trace amounts (<1% by weight) of non-aromatic organic impurities, such as higher alcohols, aldehydes, or other oxygenated compounds have little effect on the conversion reaction of this invention and may be present in the methanol feed.

In place of, or in addition to methanol, the non-aromatic reactant feed may comprise dimethyl ether. When this component is present, it can comprise up to 100% of the non-aromatic organic reactant feed or dimethyl ether can be admixed with methanol to form the non-aromatic reactant feed. For purposes of the present invention, it is contemplated to directly convert methanol and/or methyl ether in the feed to a hydrocarbon mixture characterized by a high content of light olefins, especially ethylene.

The aromatic portion of the feedstock can come from a wide variety of sources. Initially, during start-up an external aromatics source of $C_9$ aromatics and/or $C_{9+}$ aromatics (which includes $C_9$ or higher aromatics) may be co-fed with the oxygenate feed, e.g., a $C_{9+}$ reformate stream. External aromatics sources such as streams containing benzene and/or toluene can also be used to replace or supplement the external aromatics source during process start-up.

Even substantial amounts of non-aromatic organic components have little impact on the catalytic role of the aromatic co-feed. For this reason, any organic feedstream containing >10 wt. % $C_9$ or $C_{9+}$ aromatics, which have a critical diameter less than the pore size of the catalyst so as to be able to easily diffuse into the catalyst pores, is suitable for use as an initial co-feed in the process of the invention. These include, but are not limited to steam cracked naphtha or any distilled fraction thereof, $C_{9+}$ reformate streams, full-range reformates or any distilled fraction thereof, coker naphtha or any distilled fraction thereof, FCC naphtha or any distilled fraction thereof, and coal derived aromatics. The presence of impurities, such as nitrogen and sulfur compounds, dienes and styrenes, in the aromatic component can be tolerated with little impact when fluid or moving bed embodiments of the invention are employed.

After the initial start-up, the desired $C_9$ or $C_{9+}$ aromatics-containing co-feed can be derived in whole or in part from aromatics produced in the reactor by aromatization of the methanol feed.

In a preferred embodiment of the present invention, the 1 to 3 wt. % desired aromatic co-feed is comprised entirely of $C_9$ or $C_{9+}$ aromatics which are recycled from the bottom of a xylenes distillation tower.

The molar ratio of methanol and/or dimethyl ether to aromatic compound will normally be greater than 5:1, since higher concentrations of aromatic compound lead to excessive coking, increased volumes of separation and recycle traffic and minimal gains in total chemical selectivities. Moreover the molar ratio of methanol and/or dimethyl ether to aromatic compound is normally maintained below 300:1, since lower concentrations of aromatic compound lead to little or no noticeable improvement in the ethylene selectivity of the process. Preferably the molar ratio of methanol and/or dimethyl ether to aromatic compound is from 5:1 to 250:1.

The catalyst employed in the process of the invention is a porous crystalline material which has a pore size greater than the critical diameter of the aromatic compound co-feed. Preferred catalysts are porous crystalline materials having a pore size between 5 and 7 Angstrom and in particular intermediate pore size, aluminosilicate zeolites. One common definition for intermediate pore zeolites involves the Constraint Index test described in U.S. Pat. No. 4,016,218, which is incorporated herein by reference. In this case, intermediate pore zeolites have a Constraint Index of about 1–12, as measured on the zeolite alone without the introduction of modifiers and prior to any treatment to adjust the diffusivity of the catalyst. In addition to the medium-pore size aluminosilicates, other medium pore acidic metallosilicates, such as silicoaluminophosphates (SAPOs), can be used in the process of the invention.

Particular examples of suitable medium pore zeolites include ZSM-5, ZSM-11, ZSM-12, ZSM-22, ZSM-23, ZSM-35, ZSM48, MCM-22, and SAPO-34, with ZSM-5 and ZSM-11 being particularly preferred.

Zeolite ZSM-5 and the conventional preparation thereof are described in U.S. Pat. No. 3,702,886, the disclosure of which is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4.076,842, the disclosure of which is incorporated herein by reference. Zeolite ZSM-35 and the conventional preparation thereof are described in U.S. Pat. No. 4,016,245, the disclosure of which is incorporated herein by reference. ZSM48 and the conventional preparation thereof is taught by U.S. Pat. No. 4,375,573, the disclosure of which is incorporated herein by reference. MCM-22 is disclosed in U.S. Pat. No. 5,304,698 to Husain; U.S. Pat. No. 5,250,277 to Kresge et al.; U.S. Pat. No. 5,095,167 to Christensen; and U.S. Pat. No. 5,043,503 to Del Rossi et al., the disclosure of which patents are incorporated by reference.

In order to increase the concentration of aromatics in the catalyst pores without increasing the aromatic to methanol molar ratio, it may be desirable to use a catalyst having increased diffusional barriers. In particular, it may be desirable to employ a catalyst which comprises a porous crystalline material having a Diffusion Parameter for 2,2-dimethylbutane of about 0.1 $sec^{-1}$ to about 20 sect, preferably 0.1 $sec^{-1}$ to about 15 $sec^{-1}$ and most preferably 0.2 $sec^{-1}$ to about 5 $sec^{-1}$ when measured at a temperature of 120° C. and a 2,2-dimethylbutane pressure of 60 torr (8 kPa).

As used herein, the Diffusion Parameter of a particular porous crystalline material is defined as $D/r^2 \times 10_6$, wherein D is the diffusion coefficient ($cm^2/sec$) and r is the crystal radius (cm). The required diffusion parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading and is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The intermediate pore zeolites described above as being preferred for the process of the invention may have Diffusion Parameter values in excess of the required 0.1 $sec^{-1}$ to 20 $sec^{-1}$ range. However, depending on the diffusivity required in the catalyst, the Diffusion Parameter can be controlled or modified to the required value by a variety of methods. Where only limited diffusional constraint is required, such that the Diffusion Parameter is between 5 and 20 $sec^{-1}$ range, this may be achievable by using large crystal forms (greater than 1 micron) of the porous crystalline material, by depositing coke on the material prior to use in the process (as described in U.S. Pat. No. 4,097,543) and/or by combining the material with at least one oxide modifier, preferably selected from the group consisting of oxides of boron, magnesium, calcium, silicon, lanthanum and most preferably phosphorus. The total amount of coke or oxide modifier, as measured on an elemental basis, may be between about 0.05 wt. % and about 20 wt. %, and preferably is between about 1 wt. % and about 10 wt. %, based on the weight of the final catalyst.

Where a more severe diffusional constraint is required, such that the Diffusion Parameter is between 0.1 $sec^{-1}$ and <5 $sec^{-1}$ range, this may be achieved by severely steaming the catalyst so as to effect a controlled reduction in the micropore volume of the catalyst to not less than 50%, and preferably to 50% to 90%, of that of the unsteamed catalyst. Reduction in micropore volume is derived by measuring the n-hexane adsorption capacity of the catalyst, before and after steaming, at 90° C. and 75 torr n-hexane pressure. Steaming of the porous crystalline material is effected at a temperature of at least about 850° C., preferably about 950° C. to about 1075° C., and most preferably about 1000° C. to about 1050° C. for about 10 minutes to about 10 hours, preferably from 30 minutes to 5 hours. To effect the desired controlled reduction in diffusivity and micropore volume, it may be desirable to combine the porous crystalline material, prior to steaming, with a phosphorus modifier. The total amount of phosphorus modifier, which will normally be present in the catalyst in oxide form, as measured on an elemental basis, may be about 0.05 wt. % to about 20 wt. %, and preferably is from about 1 wt. % to about 10 wt. %, based on the weight of the final catalyst.

Where the modifier is phosphorus, incorporation of modifier in the catalyst of the invention is conveniently achieved by the methods described in U.S. Pat. Nos. 4,356,338, 5,110,776 and 5,231,064, the entire disclosures of which are incorporated herein by reference. Similar techniques known in the art can be used to incorporate other modifying oxides into the catalyst of the invention.

The porous crystalline material employed in the process of the invention may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, from about 2 wt. % to about 80 wt. % of the composite.

Preferably, the binder material comprises silica or a kaolin clay.

Procedures for preparing silica-bound zeolites, such as ZSM-5, are described in U.S. Pat. Nos. 4,582,815; 5,053,374; and 5,182,242. A particular procedure for binding ZSM-5 with a silica binder involves an extrusion process.

The porous crystalline material may be combined with a binder in the form of a fluidized bed catalyst. This fluidized bed catalyst may comprise clay in the binder thereof, and may be formed by a spray-drying process to form catalyst particles having a particle size of 20 microns to 200 microns.

The catalyst employed of the invention preferably has a very low acid activity. Using the alpha test of acid activity disclosed in *Journal of Catalysis*, volume 61, page 395 (1980), the entire disclosure of which is incorporated by reference herein, the catalyst of the invention preferably has an alpha value less than 50, more preferably less than 10.

The process of the invention is preferably carried out in a moving or fluid catalyst bed with continuous oxidative regeneration. The extent of coke loading can then be continuously controlled by varying the severity and/or the frequency of regeneration.

The process of the present invention is conducted at a relatively high temperature between about 350° C. and 480° C., preferably between about 400° C. and 460° C., since, as will be illustrated by the following Examples and contrary to the teaching in U.S. Pat. No. 4,499,314, we have found that such a temperature range is critical to the selective production of lower olefins. While not wishing to be bound by any theory of operation, we believe that such a relatively high temperature is essential to the skeletal isomerization and cracking of the polymethylbenzene intermediates produced, whereas higher temperatures lead to excessive coking.

The process of the invention is advantageous in that it is found that the lower olefin selectivity of the product is generally independent of methanol partial pressure so that the necessity in prior art processes to reduce the methanol pressure by the addition of diluents or by operation at reduced pressure can be avoided. The ability to operate at higher methanol partial pressures also allows the absolute yield per pass of olefin product to be increased. A suitable methanol partial pressure for use in the process of the invention is in excess of 10 psia (70 kPa), preferably 15 psia to 150 psia.

In addition, it is desirable that the conversion conditions are controlled so that the methanol conversion level is less than about 90% and preferably less than 80% since, at higher conversion levels, competing reactions to aromatics methylation, such as olefin alkylation and/or oligomerizarion to produce $C_5+$ isoolefins and/or olefin conversion to aromatics and paraffins, lower the selectivity to ethylene and propylene. Suitable control of the methanol conversion can, of course, be achieved by variation of the weight hourly space velocity, which typically can vary from about 0.1 to 100, preferably from about 0.1 to 10.

The process of the invention converts methanol and/or dimethyl ether to a light olefin stream in which ethylene comprises over 30 wt. %, and typically over 40 wt. %, of the $C_2$ to $C_4$ olefins and in which ethylene comprises more than 90 wt. %, preferably more than 95 wt. %, of the $C_2$ component. If the feedstock also contains toluene, part of the methanol will methylate the toluene to produce xylene rich in the para-isomer.

The invention will now be more particularly described in the following Examples and the accompanying drawing in which:

FIG. 1 is a process flow diagram chart for a methanol to chemicals process in accordance with the present invention.

Figure 2:
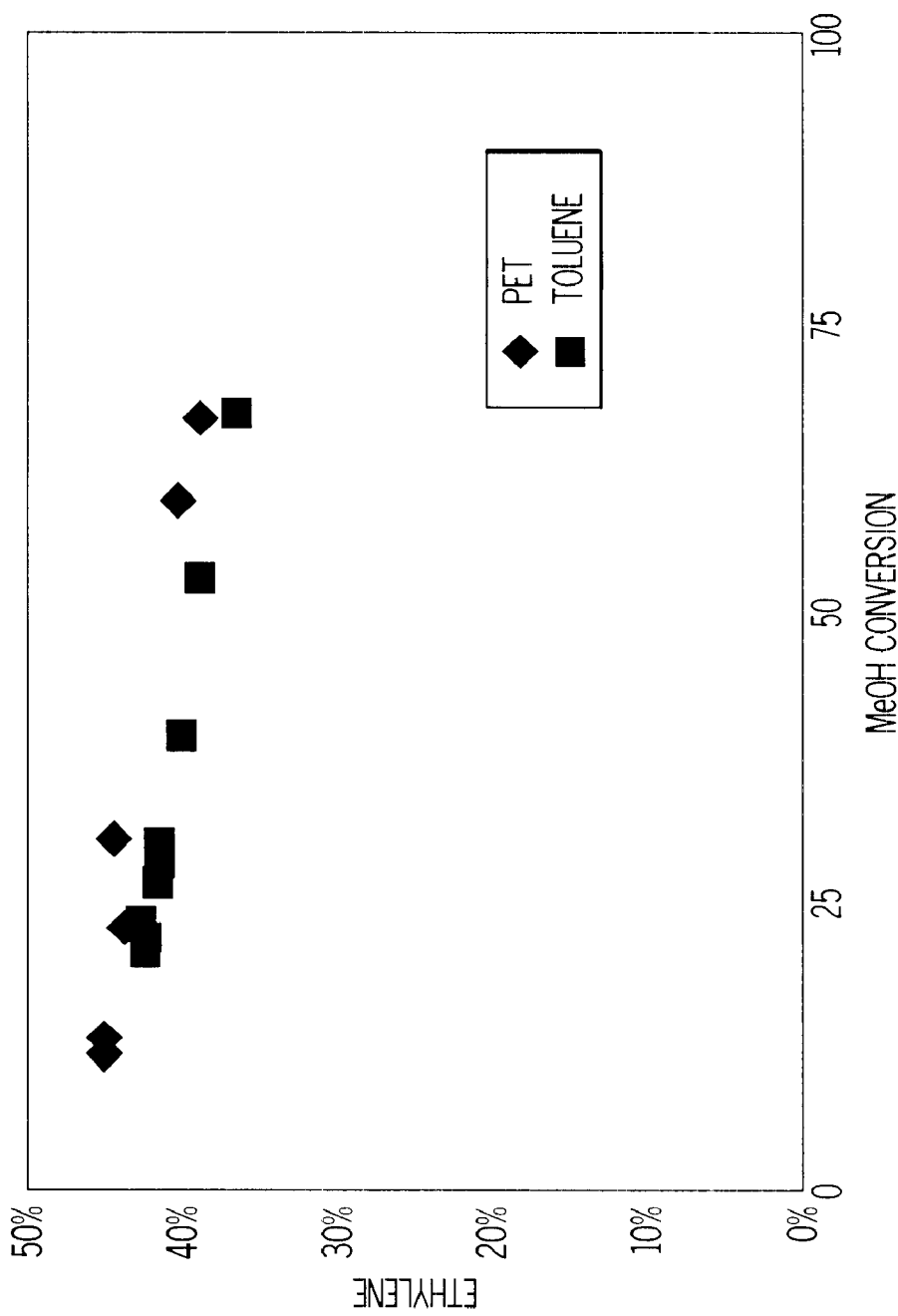

FIG. 2 compares ethylene selectivity vs. methanol conversion over a phosphorus-loaded ZSM-5, $D/r^2=0.5\times10^{-6}$ $s^{-1}$, 1 alpha catalyst using 12:1 molar methanol:aromatic feedstock, showing similar results for ethylene selectivity between toluene and para-ethyltoluene as aromatic feedstock.

In the process configuration of FIG. 1, methanol is converted to chemicals. A methanol feed 100 is introduced to a methanol converter 110 which comprises a moving or fluid catalyst bed with continuous oxidative regeneration maintained at methanol conversion conditions of 400° C. to 480° C., 35 psia to 140 psia methanol partial pressure, and 50% to 95% methanol conversion, to provide a product comprising light gas, distillable hydrocarbons, methanol and water which is directed to a separator 120. The catalyst employed can be prepared in accordance with Example 1 below. Separator overhead is passed to a compressor 130, distillable hydrocarbons are taken off the separator through line 140 to distillation column 150, and methanol and water bottoms are removed through line 160 for further treatment to separate out water. The resulting methanol can be recycled to the process through methanol feed inlet 100. Compressor 130 separates light gas products (methane, ethylene and ethane) through line 170 from distillable hydrocarbons which are routed through line 180 to distillation column 160. Distillation column 160 can separate distillable hydrocarbons into desired fractions for further processing such as propylene/propane overhead through line 190, a C4 fraction (which may also contain dimethylether) through line 200, a C5-toluene fraction through line 210, a mixed xylenes fractions through line 220, a C9+ or C10+ fraction through line 230, and a recycle line 240 through which C9 or C9+ aromatics can be recycled for combination with methanol feed 100. Line 230 can be used as a purge stream to avoid the buildup of unreactive aromatics in the recycle stream. Line 250 can be used to introduce externally supplied aromatics as described in detail above.

The mixed xylenes fractions of line 220 can be separated by a Parex or crystallizer unit 260 to provide a substantially p-xylene containing effluent stream taken off via line 270 and a mixed xylenes stream containing o-xylene, m-xylene and ethylbenzene taken off via line 280.

The C4 fraction (which may also contain dimethylether and water) may be passed via line 200 to reactor 290 wherein it is contacted with methanol and/or water supplied via line 295 to provide a substantially $C_4$ hydrocarbon stream which comprises $C_4$ olefins which is collected via line 300 and a substantially dimethylether-, methanol-, and water-containing stream which is collected via line 300 and optionally recycled to the process via line 100.

The $C_4$ hydrocarbon stream which comprises $C_4$ olefins from line 300 (or a C5 hydrocarbon-toluene fraction comprising $C_5$ olefins transferred via line 210) can be transferred to an alkylation unit 320 where it is contacted with a suitable alkylating agent, e.g., isobutane and/or isopentane, provided via line 330 under conventional alkylating conditions to provide an alkylate-containing product which is removed via line 340 and which may be used in gasoline blending.

Where the feed from line 200 or line 210 contains iso-olefins, one or more of these streams may be passed via lines 350 and 360 to an etherifier 370 wherein they are contacted with methanol etherifying agent supplied via line 380 under conventional etherification conditions. The respective tert-butyl ether or mixed tert-alkyl ether products can be removed vial line 390.

Alternately, a $C_4$ hydrocarbon-toluene fraction can be taken off column 150 via line 400, which $C_4$ hydrocarbon-toluene and dimethylether fraction comprises $C_4$–$C_6$ iso-olefins, and is passed to etherifier 370 where it is contacted with aqueous methanol under etherification conditions to provide an effluent stream which comprises an aqueous phase comprising mixed tert-alkylethers, dimethylether, methanol and water, and an organic phase comprising toluene. The phases are readily separable fraction, and the aqueous fraction containing dimethylether and methanol is recyclable to line 100.

In the Examples, micropore volume (n-hexane) measurements are made on a computer controlled (Vista/Fortran) duPont 951 Thermalgravimetric analyzer. Isotherms are measured at 90° C. and adsorption values taken at 75 torr n-hexane. The diffusion measurements are made on a TA Instruments 2950 Thermalgravimetric Analyzer equipped with a Thermal Analysis 2000 controller, a gas switching accessory and an automatic sample changer. Diffusion measurements are made at 120° C. and 60 torr 2,2-dimethylbutane. Data are plotted as uptake versus square root of time. Fixed bed catalytic testing is conducted using a ⅜" (1 cm) outside diameter, down-flow reactor equipped with a thermocouple. Methanol, water, and externally supplied aromatics and recycled aromatics are all pumped to the reactor by way of a vaporizer equipped with a static mixer to thoroughly gasify and mix the feedstocks upstream of the reactor. The reactor is equipped with a backpressure regulator to enable examination of the products at a wide variety of temperature, pressures and WHSVs. The total reactor effluent is analyzed, on line, by gas chromatography. Methanol conversion is calculated based on hydrocarbon formation only. Selectivities to hydrocarbon product are calculated on a "water free" basis.

EXAMPLE 1

Phosphoric acid, kaolin clay, and 450:1 $SiO_2/Al_2O_3$ ZSM-5 were slurried in water and spray dried to make a typical fluid-bed catalyst. The catalyst was calcined in air at 510° C. The finished catalyst contained 40 wt. % ZSM-5 and 4.5 wt. % phosphorus. This material has an n-hexane sorption of 33.5, a diffusion parameter of 27, and an alpha of about 7. The catalyst was then steamed at 1050° C. for 0.75 hours in 1 atmosphere steam to produce a final catalyst having a Diffusion Parameter of 0.46 $sec^{-1}$ and an n-hexane sorption of 30.6 mg/g.

EXAMPLE 2

A first 0.5 g sample of the steamed catalyst of Example 1 is used to convert a 12:1 molar methanol:para-ethyltoluene aromatic at 0.5 to 5 WHSV, 380° C., and 1 atm pressure. A wide range of methanol conversions was obtained. The hydrocarbon product ethylene selectivity is plotted against methanol conversion in FIG. 2.

A second 0.5 g sample of the steamed catalyst of Example 1 is used to convert a 12:1 molar methanol:toluene aromatic at 0.5 to 5 WHSV, 380° C., and 1 atm pressure. A wide range of methanol conversions was obtained. The hydrocarbon product ethylene selectivity is plotted against methanol conversion in FIG. 2 which depicts essentially identical high ethylene selectivity for both toluene and para-ethyltoluene, showing equivalence of a $C_9$ aromatic co-feed to toluene as ethylene-selective aromatic co-feeds.

EXAMPLE 3

The procedure of Example 2 was repeated at higher temperatures. A comparison of product slates and process conditions for para-ethyltoluene and toluene aromatic cofeeds at methanol conversions of about 74% is provided in the Table 1 and shows the interchangeability of para-ethyltoluene for toluene as a co-feed.

TABLE

Example: PET vs. Toluene Cofeed

| Run # | 1 | 2 |
|---|---|---|
| BedTemp, ° C. | 450 | 440 |
| Furnace T, ° C. | 450 | 440 |
| WHSV | 6.45 | 7.62 |
| TOS, minutes | 181 | 124 |
| Weight % Cofeed | 2 | 2 |
| Aromatic Cofeed | Toluene | p-ethyltoluene |
| Pressure (PSIA) | 90 | 90 |
| Composition, wt. % | | |
| Methane | 0.35 | 0.30 |
| Ethylene | 7.93 | 8.00 |
| Ethane | 0.04 | 0.04 |
| Propylene | 6.63 | 6.53 |
| Propane | 0.70 | 0.72 |
| Methanol/DME | 25.32 | 25.57 |
| Isobutene | 2.50 | 2.09 |
| Cis-2-butene | 1.20 | 1.19 |
| Trans-2-butene | 0.88 | 0.87 |
| Butanes | 1.11 | 1.25 |
| Isopentene | 0.06 | 0.07 |
| C5–C9 non-aromatics | 6.30 | 6.77 |
| Isopentane | 1.08 | 1.22 |
| Benzene | 0.12 | 0.12 |
| Heptane | 0.39 | 0.40 |
| Toluene | 0.83 | 0.38 |
| EB | 0.14 | 0.14 |
| M + p-xylene | 2.38 | 2.19 |
| o-xylene | 0.09 | 0.08 |
| p-ethyltoluene | 0.51 | 0.82 |
| 1,2,4TMB | 0.12 | 0.11 |
| C10+ | 0.38 | 0.34 |
| Water | 40.95 | 40.81 |
| p-xylene selectivity | 92.4% | 92.8% |
| Methanol Conversion | 74.17% | 73.91% |
| Cofeed Conversion | 58.5% | 59.2% |
| Methanol to: | | |
| Ethylene | 24.4% | 24.4% |
| Propylene | 20.4% | 19.9% |
| Butenes | 14.1% | 12.7% |
| C5–C9 non-aromatics | 24.1% | 25.8% |
| C1–C4 Paraffins | 6.8% | 7.0% |
| Feedstock | 1.9% | 0.5% |
| New rings | 1.4% | 9.5% |
| Total Olefins | 75.4% | 73.4% |

It is claimed:
1. A process for converting methanol and/or dimethyl ether to a product containing $C_2$ to $C_4$ olefins which comprises:
　1) contacting a feed which contains methanol and/or dimethyl ether with a catalyst comprising a porous crystalline material, said contacting step being conducted in the presence of aromatics comprising $C_9$ or $C_{9+}$ aromatic compound produced in said process under conversion conditions including a temperature of 350° C. to 480° C. and a methanol and/or dimethyl ether partial pressure in excess of 70 kPa, said porous crystalline material having a Diffusion Parameter for 2,2-dimethylbutane of about 0.1 $sec^{-1}$ to about 20 $sec^{-1}$ when measured at a temperature of 120° C. and a 2,2-dimethylbutane pressure of 60 torr (8 kPa), and the aromatics being alkylated by the methanol and/or dimethyl ether under said conversion conditions to provide a stream which contains $C_2$ to $C_4$ olefins and $C_9$ or $C_{9+}$ aromatic compound;
　2) separating said stream to form a substantially $C_2$ to $C_4$ olefin product stream and a substantially $C_9$ or $C_{9+}$ aromatic compound stream; and
　3) recycling at least a portion of said substantially $C_9$ or $C_{9+}$ aromatic compound stream to step 1.

2. The process of claim 1 wherein said porous crystalline material is selected from the group consisting of ZSM-5, ZSM-11, ZSM-12, ZSM-22, ZSM-23, ZSM-35, ZSM48, MCM-22 and SAPO-34.

3. The process of claim 1 wherein said porous crystalline material comprises ZSM-5.

4. A process for converting methanol and/or dimethyl ether to a product comprising olefins, $C_{9+}$ aromatics and non-$C_{9+}$ aromatics which comprises:
   i) combining a feedstream which contains methanol and/or dimethyl ether with a feedstream substantially comprising $C_9$ or $C_{9+}$ aromatics produced in said process to provide a mixed feed;
   ii) contacting said mixed feed in an oxygenate conversion zone with a catalyst comprising a porous crystalline material, said contacting step being conducted under conversion conditions including a temperature of 350° C. to 480° C. and a methanol and/or dimethyl ether partial pressure in excess of 70 kPa, said porous crystalline material having a pore size greater than the critical diameter of toluene, and at least some of said $C_9$ or $C_{9+}$ aromatics being alkylated by the methanol and/or dimethyl ether under said conversion conditions, to provide a product containing olefins, $C_9$ or $C_{9+}$ aromatics and non-$C_9$ or non-$C_{9+}$ aromatics;
   iii) separating $C_9$ or $C_{9+}$ aromatics from said product to provide a feedstream substantially comprising $C_9$ or $C_{9+}$ aromatics;
   iv) recycling to step i) at least some of said feedstream substantially comprising $C_9$ or $C_{9+}$ aromatics;
   v) separating said olefins from said product to provide a stream substantially comprising olefins; and
   vi) separating said non-$C_9$ or non-$C_{9+}$ aromatics from said product to provide a stream substantially comprising non-$C_9$ or non-$C_{9+}$ aromatics.

5. The process of claim 4 wherein said olefins comprise $C_2$ to $C_4$ olefins.

6. The process of claim 4 which further comprises
   vii) purging said feedstream substantially comprising $C_9$ or $C_{9+}$ aromatics to an extent sufficient to prevent undesirable accumulation of unreactive $C_{9+}$ aromatics in the mixed feed.

7. The process of claim 4 wherein the molar ratio of methanol and/or dimethyl ether to $C_9$ or $C_{9+}$ aromatics is greater than 5:1 and less than 300:1.

8. The process of claim 4 wherein said non-$C_9$ or non-$C_{9+}$ aromatics of step ii) comprise mixed xylenes which are separated out to provide a substantially mixed xylene-containing stream which is subsequently treated to provide a substantially p-xylene-containing stream.

9. The process of claim 4 wherein the conversion conditions include a temperature of 400° C. to 460° C., and a methanol and/or dimethyl ether conversion rate of less than 90%.

10. The process of claim 4 wherein the porous crystalline material has a pore size of 5 to 7 Angstroms.

11. The process of claim 4 wherein the porous crystalline material is selected from the group consisting of ZSM-5, ZSM-11, ZSM-12, ZSM-22, ZSM-23, ZSM-35, ZSM-48, MCM-22 and SAPO-34.

12. The process of claim 4 wherein the porous crystalline material has a Diffusion Parameter for 2,2-dimethylbutane of about 0.1 sec$^{-1}$ to about 20 sec$^{-1}$ when measured at a temperature of 120° C. and a 2,2-dimethylbutane pressure of 8 kPa.

13. The process of claim 4 wherein the porous crystalline material has a Diffusion Parameter for 2,2-dimethylbutane of about 0.2 sec$^{-1}$ to about 5 sec$^{-1}$ when measured at a temperature of 120° C. and a 2,2-dimethylbutane pressure of 8 kPa.

14. The process of claim 4 wherein the catalyst has an alpha value less than 10 and contains coke or an oxide modifier selected from the group consisting of oxides of boron, magnesium, silicon and phosphorus.

15. A process for converting methanol and optionally dimethyl ether to a product comprising olefins, $C_{9+}$ aromatics and non-$C_{9+}$ aromatics which comprises:
   a) combining a feedstream which contains methanol and optionally dimethyl ether with a feedstream substantially comprising $C_9$ or $C_{9+}$ aromatics produced in said process to provide a mixed feed;
   b) contacting said mixed feed in an oxygenate conversion zone with a catalyst comprising a porous crystalline material, said contacting step being conducted under conversion conditions including a temperature of 350° C. to 480° C. and a methanol and optionally dimethyl ether partial pressure in excess of 70 kPa, said porous crystalline material having a pore size greater than the critical diameter of toluene, and at least some of said $C_9$ or $C_{9-}$ aromatics being alkylated by the methanol, and optionally dimethyl ether under said conversion conditions, to provide a product containing olefins, $C_9$ or $C_{9+}$ aromatics and non-$C_9$ or non-$C_{9+}$ aromatics;
   c) separating the product from said conversion zone into a light gas hydrocarbon fraction, a distillable hydrocarbon fraction, and an aqueous methanol fraction;
   d) recycling said aqueous methanol fraction to step a);
   e) compressing said light gas hydrocarbon fraction to provide a $C_1$–$C_2$ hydrocarbon fraction and $C_{3+}$ hydrocarbon fraction;
   f) collecting said $C_1$–$C_2$ hydrocarbon fraction;
   g) introducing said $C_{3+}$ hydrocarbon fraction and said distillable hydrocarbon fraction to a distillation column and withdrawing a $C_3$ hydrocarbon overheads fraction, a $C_4$ hydrocarbon and dimethyl ether fraction, a $C_5$ hydrocarbon-toluene fraction, a mixed xylenes fraction, a $C_9$ aromatics fraction and a $C_{10+}$ aromatics fraction;
   h) treating said $C_4$ hydrocarbon and dimethylether fraction with water and/or said aqueous methanol to provide a substantially $C_4$ hydrocarbon stream which comprises $C_4$ olefins and a substantially dimethylether-, methanol-, and water-containing stream;
   i) recycling said substantially dimethylether-, methanol-, and water-containing stream to step a); and
   j) treating said mixed xylenes fraction to provide a substantially p-xylene containing effluent stream and a mixed xylenes-containing effluent stream substantially comprising ethylbenzene, o-xylene and m-xylene.

16. The process of claim 15 which comprises alkylating said substantially $C_4$ hydrocarbon stream containing $C_4$ olefins by contacting with an alkylating agent selected from the group consisting of isobutane and isopentane under olefin alkylating conditions to provide an alkylate-containing product.

17. The process of claim 15 which comprises alkylating said $C_5$ hydrocarbon-toluene fraction containing $C_5$ olefins by contacting with an alkylating agent selected from the group consisting of isobutane and isopentane under olefin alkylating conditions to provide an alkylate-containing product.

18. The process of claim 15 which comprises etherifying said $C_4$ hydrocarbon stream containing $C_4$ iso-olefins by contacting with methanol etherifying agent under etherification conditions to provide a product containing tert-butyl ether.

19. The process of claim 15 which comprises etherifying said $C_5$ hydrocarbon-toluene fraction, containing $C_5$ iso-olefins and $C_6$ iso-olefins, by contacting with methanol etherifying agent under etherification conditions to provide a product containing mixed tert-alkyl ethers.

20. A process for converting methanol and optionally dimethyl ether to a product comprising olefins, $C_{9+}$ aromatics and non-$C_{9+}$ aromatics which comprises:
   A) combining a feedstream which contains methanol and optionally dimethyl ether with a feedstream substantially comprising $C_9$ or $C_{9+}$ aromatics produced in said process to provide a mixed feed;
   B) contacting said mixed feed in an oxygenate conversion zone with a catalyst comprising a porous crystalline material, said contacting step being conducted under conversion conditions including a temperature of 350° C. to 480° C. and a methanol and optionally dimethyl ether partial pressure in excess of 70 kPa, said porous crystalline material having a pore size greater than the critical diameter of toluene, and at least some of said $C_9$ or $C_{9+}$ aromatics being alkylated by the methanol and optionally dimethyl ether under said conversion conditions, to provide a product containing olefins, $C_9$ or $C_{9+}$ aromatics and non-$C_9$ or non-$C_{9+}$ aromatics;
   C) separating the product from said conversion zone into a light gas hydrocarbon fraction, a distillable hydrocarbon fraction, and an aqueous methanol fraction;
   D) recycling at least a portion of said aqueous methanol fraction to step A);
   E) compressing said light gas hydrocarbon fraction to provide a $C_1$–$C_2$ hydrocarbon fraction and $C_{3+}$ hydrocarbon fraction;
   F) collecting said $C_1$–$C_2$ hydrocarbon fraction;
   G) introducing said $C_{3+}$ hydrocarbon fraction and said distillable hydrocarbon fraction to a distillation column and withdrawing a $C_3$ hydrocarbon overheads fraction, a $C_4$ hydrocarbon-toluene and dimethyl ether fraction comprising $C_4$–$C_6$ iso-olefins, a mixed xylenes fraction, a $C_9$ aromatics fraction and a $C_{10+}$ aromatics fraction;
   H) etherifying said $C_4$ hydrocarbon-toluene and dimethylether fraction comprising $C_4$–$C_6$ iso-olefins by contacting with aqueous methanol under etherification conditions to provide an effluent stream which comprises an aqueous phase comprising mixed tert-alkylethers, dimethylether, methanol and water, and an organic phase comprising toluene which is recyclable to step A); and
   I) separating said aqueous phase into a substantially mixed tert-alkylether fraction, and a dimethylether-, methanol- and water-containing fraction which is recyclable to step A).

21. A process for converting methanol and/or dimethyl ether to a product containing olefin, $C_{9+}$ aromatics and non-$C_{9+}$ aromatics which comprises:
   i) combining a feedstream which contains methanol and/or dimethyl ether with a feedstream substantially comprising $C_9$ or $C_{9+}$ aromatics produced in said process to provide a mixed feed;
   ii) contacting said mixed feed in an oxygenate conversion zone with a catalyst comprising a porous crystalline material, said contacting step being conducted under conversion conditions including a temperature of 350° C. to 480° C. and a methanol and/or dimethyl ether partial pressure in excess of 10 psia, said porous crystalline material having a pore size greater than the critical diameter of toluene and the toluene being capable of alkylation by the methanol and/or dimethyl ether under said conversion conditions to provide a product containing olefins, $C_{9+}$ aromatics and non-$C_{9+}$ aromatics;
   iii) separating out from said product $C_9$ or $C_{9+}$ aromatics to provide a feedstream substantially comprising $C_9$ or $C_{9+}$ aromatics;
   iv) recycling to step i) at least some of said feedstream substantially comprising $C_9$ or $C_{9+}$ aromatics; and
   v) collecting said olefins and said non-$C_9$ or non-$C_{9+}$ aromatics.

22. The process of claim 21 wherein said olefins comprise $C_2$ to $C_4$ olefins.

23. The process of claim 21 which further comprises
   vi) purging said feedstream substantially comprising $C_9$ or $C_{9+}$ aromatics to an extent sufficient to prevent undesirable accumulation of unreactive $C_{9+}$ aromatics.

24. The process of claim 21 wherein the molar ratio of methanol and/or dimethyl ether to $C_9$ or $C_{9+}$ aromatics is greater than 5:1 and less than 300:1.

25. The process of claim 21 wherein the molar ratio of methanol and/or dimethyl ether to $C_9$ or $C_{9+}$ aromatics is from 5:1 to 150:1.

26. The process of claim 21 wherein the conversion conditions include a temperature of 400° C. to 460° C.

27. The process of claim 21 wherein the conversion conditions are such that the methanol and/or dimethyl ether conversion rate is less than 90%.

28. The process of claim 21 wherein the porous crystalline material has a pore size between 5 and 7 Angstroms.

29. The process of claim 21 wherein the porous crystalline material is ZSM-5.

30. The process of claim 21 wherein the porous crystalline material has a Diffusion Parameter for 2,2-dimethylbutane of about 0.1–20 sec$^{-1}$ when measured at a temperature of 120° C. and a 2,2-dimethylbutane pressure of 60 torr.

31. The process of claim 21 wherein the porous crystalline material has a Diffusion Parameter for 2,2-dimethylbutane of about 0.2–5 sec$^{-1}$ when measured at a temperature of 120° C. and a 2,2-dimethylbutane pressure of 60 torr.

32. The process of claim 21 wherein the catalyst has an alpha value less than 50.

33. The process of claim 21 wherein the catalyst has an alpha value less than 10.

34. The process of claim 21 wherein the catalyst contains coke or an oxide modifier selected from the group consisting of oxides of boron, magnesium, silicon and phosphorus.

35. The process of claim 34 wherein the catalyst contains about 0.05 to about 20 wt. % of the coke or the oxide modifier on an elemental basis.

36. The process of claim 34 wherein the catalyst contains about 1 to about 10 wt. % of the coke or the oxide modifier on an elemental basis.

* * * * *